(12) United States Patent
Van Der Hulst et al.

(10) Patent No.: US 11,298,048 B2
(45) Date of Patent: Apr. 12, 2022

(54) SLEEP POSITION TRAINER WITH NON-MOVEMENT TIMER

(71) Applicant: NIGHTBALANCE B.V., Eindhoven (NL)

(72) Inventors: Robert Franciscus Van Der Hulst, Eindhoven (NL); Thijs Van Oorschot, Eindhoven (NL); Eline Christiane Van Beest, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 190 days.

(21) Appl. No.: 16/498,683

(22) PCT Filed: Mar. 29, 2018

(86) PCT No.: PCT/NL2018/050195
§ 371 (c)(1),
(2) Date: Sep. 27, 2019

(87) PCT Pub. No.: WO2018/182414
PCT Pub. Date: Oct. 4, 2018

(65) Prior Publication Data
US 2020/0100707 A1 Apr. 2, 2020

(30) Foreign Application Priority Data

Mar. 29, 2017 (NL) ..................................... 2018593
Mar. 29, 2017 (NL) ..................................... 2018594
Mar. 29, 2017 (NL) ..................................... 2018596

(51) Int. Cl.
*A61B 5/11* (2006.01)
*A61B 5/00* (2006.01)

(52) U.S. Cl.
CPC ........... *A61B 5/1116* (2013.01); *A61B 5/1126* (2013.01); *A61B 5/486* (2013.01);
(Continued)

(58) Field of Classification Search
None
See application file for complete search history.

(56) References Cited

U.S. PATENT DOCUMENTS 8,803,682 B2   8/2014   Wong
2010/0010390 A1*   1/2010   Skelton ................. A61B 5/1116
600/595

(Continued)

FOREIGN PATENT DOCUMENTS

WO   2011039141 A1   4/2011
WO   2013129924 A2   9/2013

OTHER PUBLICATIONS

International Search Report and Written Opinion, International Application No. PCT/NL2018/050195, dated Oct. 4, 2018.

*Primary Examiner* — Daniel L Cerioni
*Assistant Examiner* — Raymond P Dulman

(57) ABSTRACT

A sleep position trainer (1) has a normal operational mode for alerting when a posture of the body detected by the position sensor (34) corresponds with an undesired body posture. The sleep position trainer further comprises a non-movement timer (t1) for timing a non-movement period of the user wearing the sleep position trainer. An output signal is send to an alert unit in case that a posture of the body detected by a position sensor (34) corresponds with a body posture when a threshold value of the non-movement timer (t1) of at least 15 minutes is exceeded.

8 Claims, 4 Drawing Sheets

(52) U.S. Cl.
CPC .......... *A61B 5/4815* (2013.01); *A61B 5/4818* (2013.01); *A61B 5/746* (2013.01); *A61B 5/7455* (2013.01); *A61B 2562/0219* (2013.01)

(56) References Cited

U.S. PATENT DOCUMENTS

| | | |
|---|---|---|
| 2011/0112442 A1 | 5/2011 | Meger et al. |
| 2012/0132211 A1 | 5/2012 | Halperin et al. |
| 2016/0073935 A1 | 3/2016 | van Beest |
| 2016/0374608 A1* | 12/2016 | Dugan .................. A61B 5/1114 600/301 |

* cited by examiner

Legend:
- – – 30 minutes
- – · – 60 minutes
- —— 90 minutes

I T=0

II T=30

III T=60

IV T=90

V T=105

VI T=120

VII T=150

VIII T=180

IX

SLEEP POSITION TRAINER WITH NON-MOVEMENT TIMER

CROSS-REFERENCE TO PRIOR APPLICATIONS

This application is the U.S. National Phase application under 35 U.S.C. § 371 of International Application Serial No. PCT/NL2018/050195, filed on 29 Mar. 2018, which claims the benefit of Dutch Application Serial Numbers 2018593, filed on 29 Mar. 2017, U.S. Pat. No. 2,018,594, filed on 29 Mar. 2017 and U.S. Pat. No. 2,018,596, filed on 29 Mar. 2017. These applications are hereby incorporated by reference herein.

The present invention relates to a sleep position trainer. The sleep position trainer is arranged to provide an alert during a person's sleep in response to a received signal from a position sensor of the sleep position trainer. The sleep position trainer is arranged to provide an alert during a person's sleep in response to a received signal from the position sensor to stimulate a user to change a sleep position.

WO2011/39141A1 discloses a sleep posture alerting apparatus to be worn on a body of a user. The apparatus comprises an electronic control unit and a sensor operatively connected to the control unit for detecting a body posture of the user. The apparatus further comprises an alarming device which is operatively connected to the control unit. When in a normal operational mode of the apparatus, the sensor detects a body posture which exits a predefined posture range, the control unit outputs an alarm signal to the alarm device. The alarm device receives the signal from the control unit and generates an alarm.

The disclosed sleep posture alerting apparatus may be provided with a memory to store detected and measured events. Registering events makes it possible to gather information about a user's sleep. The user's sleep information can be used at another moment in time to determine, inform, diagnose, help and/or advise users or others of various elements to improve compliance to a sleep treatment protocol.

The sleep posture apparatus may be supplied to a user in combination with a software program which can be loaded on a personal computer. The software program may be used to download, store, analyse, display, visualise and/or transfer data from the sleep posture apparatus to the computer. The software program enables the interpretation, visualisation and comparison of the events and data stored by the apparatus to obtain insight in sleep events. Users can be informed about their sleep behaviour to guide and train the user into sleeping with an improved sleeping posture and to stimulate the use of the apparatus.

WO2013/129924A2 discloses a further improved sleeping posture apparatus, wherein the alarming device is configured to generate different alarm stimuli. The control unit is programmed to send an alarm signal to the alarming device such that a stimulus variation is effected by the alarming device. Instead of providing the same stimulus, a stimulus variation is used in order to prevent a habituation effect. The stimulus variation can comprise a variation in strength or amplitude of the stimulus. The stimulus variation can comprise a variation in a length of a stimulus and/or in a frequency of the stimulus.

Further, it is disclosed that different users show and/or experience different optimal nightly stimuli. To accustom individual stimulus optimisation, stimulus types, levels, frequencies strengths, lengths, locations, amplitudes and/or interstimulus intervals can be adapted towards the optimal subject reaction.

The improved sleeping posture apparatus which features a stimulus variation may prevent habituation and may optimise a user's reaction which may contribute to an improved compliance to a sleep disorder treatment protocol. A drawback of this sleep posture apparatus is that it still does not optimally satisfy to specific user needs.

It is an object of the invention to provide an improved sleep posture alerting apparatus, also called a sleep position trainer apparatus or shortly indicated as a sleep position trainer, a SPT, a sleep posture alerting apparatus or a sleep posture trainer.

According to the invention, a sleep position trainer apparatus is provided for improving a sleep quality of a user by avoiding an undesired body posture during a sleep period. The sleep position trainer apparatus, also called shortly a sleep position trainer, is in particular suitable to be used in a sleep disorder treatment, e.g. in an apnoea treatment.

The sleep position trainer apparatus comprises a control unit. The control unit includes a control programme which is programmed to generate an output signal based on at least one received input signal.

The sleep position trainer apparatus comprises at least one sensor for detecting a sleep related event. The sensor is operatively connected to the control unit to provide a sensor signal as a first input signal to the control unit.

The sleep position trainer apparatus comprises an alert unit for providing an alert to the user wearing the sleep position trainer. The alert unit is operatively connected to the control unit to receive the generated output signal from the control unit, whereafter an alert stimulus is provided.

The sleep position trainer comprises a position sensor for detecting a body posture of a person wearing the sleep position trainer. The sleep position trainer is adapted to train a person to sleep in permitted sleep positions, or so called sleep body postures.

The sleep position trainer has a normal operational mode for alerting a user during a sleep period. In the normal operational mode, the control unit generates an output signal to the alert unit, and the alert unit generates an alert stimulus when a posture of the body detected by the position sensor corresponds with at least one predefined undesired posture. Laying in the predefined body posture is in a sleep position training defined as a sleep related event. In setting the control programme, a sleep position may be selected and predetermined as an undesired body posture. Laying in the predetermined undesired body posture, e.g. a supine position, may adversely affect a sleep quality. For example, laying in the supine position during a sleep period may increase a risk on an apnoea and for that reason the supine position may be predefined as the undesired sleep posture. By detecting the undesired sleep posture, such a negative consequence of the sleep related event may be prevented.

According to a first aspect of the invention, the sleep position trainer further comprises a non-movement timer for timing a non-movement period of the user wearing the sleep position trainer, wherein the control unit is programmed to send an output signal to the alert unit when a posture of the body detected by the body position sensor which corresponds to a posture other than the at least one predefined undesired posture, e.g. a supine position, in case that a threshold value of at least 15 minutes, in particular at least 30 minutes, of the non-movement timer is exceeded.

The sleep position trainer including the non-movement timer advantageously may prevent a user to lay too long in the same position which may reduce relating physical problems, like neck and shoulder complaints. The sleep position trainer including the non-movement timer stimulates a timely posture change during a sleep period, such that a proper blood circulation is stimulated during a sleep period.

The sleep position trainer including the non-movement timer may advantageously contribute to an improved compliance to a sleep disorder treatment protocol by eliminating secondary phenomena. By alerting the user during a sleep period when the user is laying in an undesired posture, the sleep position trainer stimulates a user to lay in a several allowed positions. In the allowed positions, the user may be less vulnerable to undesired sleep events relating to a sleep disorder, e.g. snoring or an occurrence of an apnoea. However, without the feature of the non-movement timer, in such a sleep position treatment, some users may tend to lay in just a few or even a single posture. These postures are individually preferred by the user. This user tendency may lead to laying for a long time in a same position which may cause physical problems. Such users may initially be helped by reducing sleep disorders, but without the feature of the non-movement timer for desired postures, the user may later on suffer from neck and shoulder complaints. Complaints of stiffness, painful hips or even bedsores or other medical problems may come up. The non-movement timer of the sleep position trainer may reduce or prevent negative side effects in a sleep therapy when keeping a person away from an undesired sleeping position. Advantageously, the sleep position trainer including the feature of a non-movement timer contributes to a compliance to a treatment protocol by timely activating users to change position during a sleep period.

In an embodiment of the sleep position trainer according to the invention, the threshold value of the non-movement timer is a predetermined threshold value. The predetermined threshold value may for example be set at 15 or 30 minutes for a duration of a non-movement period in a permitted sleep position. A threshold value of at least 15 minutes may effectively reduce non-movement related physical problems. Advantageously, a threshold value of at least 30 minutes contributes to a balanced distribution of sleep postures during a sleep period. The predetermined threshold value may be programmed as a general threshold value for all users of the sleep position trainer.

In an embodiment of the sleep position trainer according to the invention, the threshold value of the non-movement timer is a constant value during a sleep period. Preferably, the threshold value of the non-movement timer is a varying, a non-constant, threshold value during a sleep period.

In a particular embodiment, the at least one threshold value of the non-movement timer is adapted in dependence of a progression of a sleep period. Advantageously, by adapting the threshold value during a sleep period, a routine for preventing a too long duration of non-movement in a certain posture may start in a mitigated manner and may if required become more strict at a later stage of a sleep period. For example, the at least one threshold value may be adapted after a progression of a half-time of a sleep period, e.g. estimated and set at a lapsed time of four hours, such that a permitted duration of non-movement is set to a shorter time duration for a second half-time of the sleep period. Such a smaller value of the threshold value may prevent a user to sleep too long in a certain posture when taking into account a whole sleep period. Advantageously, the sleep position trainer stimulates a more equally distribution of postures of a user during a sleep period.

In an embodiment of the sleep position trainer according to the invention, the sleep position trainer further comprises a memory for storing user sleep data which user sleep data contains personal sleep data of an individual user. The control unit is programmed to derive an alert criterion from the user sleep data to determine whether or not an alert stimulus is to be generated and whether or not the output signal is to be send to the alert unit. The user sleep data contains non-movement data of an individual user. The non-movement data determines a permitted duration of a non-movement period of the user in a certain posture during a sleep period. The alert criterion derived from the non-movement data determines whether or not the output signal is to be sent to the alert unit. The non-movement data is user specific which has an advantage in that a due account can be taken for a particular condition of the user. If for example, the user has a bedsore at a body part, a particular posture in which the user lays on the bedsore may be avoided by setting the non-movement data at a short or even zero duration for that particular posture.

In an embodiment of the sleep position trainer according to the invention, the non-movement data may be specified for at least one posture of the user. The non-movement data may include at least one threshold value for the non-movement timer corresponding to at least one user posture. Advantageously, different threshold values may be set for different postures of the user. Herewith, the sleep position trainer may be configured accurately to a user specific needs which will contribute to a compliance to a sleep disorder treatment protocol.

In an embodiment of the sleep position trainer, the user sleep data contains non-movement data of an individual user determining a permitted duration of a period of non-movement of the user in a certain posture during a sleep period. The control unit is programmed to derive an alert criterion from the non-movement data. The alert criterion may determine a time period of non-movement, after which time period an alert stimulus may be generated. When the user is remaining too long in a certain position, an alert stimulus is generated by the alert unit to activate the user. Here, a period of non-movement means a period in which a user is laying in the same posture, e.g. too long in a prone, supine or side position. Advantageously, the sleep position trainer according to the invention may improve sleep quality by preventing a user to stay too long in the same posture.

In an embodiment of the sleep position trainer according to the invention, the at least one threshold value is adapted in dependence of recorded previous postures during a sleep period of a person. Occurring postures during a sleep period are recorded and the at least one threshold value is adapted in dependence of these recorded postures, such that the user is stimulated to sleep in different postures during the sleep period.

In a particular embodiment, a number of times of a presence of a certain posture during a sleep period may be decisive for setting the at least one threshold value during the sleep period. In further particular embodiment, an amount of time in a certain posture during a sleep period may be recorded and may be decisive for setting the at least one threshold value during the sleep period. When a certain posture appears to be present for many times during a sleep period, a user apparently tend to lay often in that certain posture which may be undesirable. By reducing the at least one threshold value for that certain posture, the user is stimulated to refrain from that certain posture for a longer period during the sleep period.

Generally, a sleep period has a starting point in which a person falls asleep and an end point in which a person is awake and ready to get out of bed. The sleep period has a duration from the starting point to the endpoint. Generally, a sleep period has a duration of about 6 to 9 hours. A duration of a sleep period is user dependent. In an embodiment of the sleep position trainer, the at least one threshold value of the non-movement data is related to a duration of a sleep period of the particular user.

In an embodiment of the sleep position trainer, the at least one threshold value which is initially set at an initial value is adaptable in dependence of a response of the user to a generated stimulus caused by an excess of a previous threshold value. The adapted threshold value may be set to a short duration e.g. of at most 15 minutes, preferably at most 5 minutes, to prevent a too early return to the previous posture for which the user was alerted. Advantageously, the adapted threshold value may prevent a frequent return to a same posture.

For example, an initial threshold value may be set at a 30 minutes duration for a non-movement in a left sided sleep position. After exceeding this 30 minutes threshold value, the user may change for 10 minutes to another sleep position and may then return again to the left-sided sleep position. As the user was only for a relatively short time period away from the left-sided sleep position, it is intended to prevent the user to remain again for 30 minutes in this left-sided sleep position. Advantageously, the initial threshold value is adapted to a shorter duration, e.g. 5 or 10 minutes, or even 0 minutes, to prevent the user to frequently return and stay too long in the left-sided sleep position during a total sleep period. Preferably, a threshold value, no matter whether it is an initial threshold value or an adapted threshold value, always has a minimum value of at least 5 minutes, in particular at least 15 minutes, to prevent over-stimulation. Advantageously, the adapted threshold value which is shorter than the previous threshold value may contribute to a more balanced schedule of sleep positions during a sleep period.

In an embodiment of the sleep position trainer, a threshold value of the non-movement timer is initially set for a certain posture in advance of a sleep period and during the sleep period adaptable by taking into account a duration of being away from said certain posture. Based on the duration of laying in another position, the threshold value may be adapted within a range from a short period of a few minutes to a relatively long period of 15 or 30 minutes, in particular to the duration which is defined by the initial threshold value.

Preferably, a first adapted threshold value regarding duration in a certain posture is equal to the initial set threshold value minus a first timed duration of the user lying in said posture, such that the first adapted threshold value equals an initially permitted remaining duration for said posture at a moment of a change of a posture. Subsequently, in case that the user stays away for a second timed duration from said posture, the first adapted threshold value is adapted to a second adapted threshold value by adding the second timed duration. Preferably, the second timed duration is added to the remaining duration until the initial set threshold value is reached. Advantageously, the non-movement timer is automatically set by this routine to achieve a balanced distribution of sleep postures during a sleep period.

For example, an initial threshold value may be set at a 30 minutes duration for a non-movement in a left-sided sleep position. When exceeding the 30 minutes, the user is alerted. From the moment that the user is no longer in the left-sided sleep position, the threshold value is adapted and increases from 0 minutes to 30 minutes during a time that the user remains away from the left-sided sleep position. When being away from this sleep position for only 10 minutes, the threshold value will be adapted by 10 minutes which permits the user to lay again in the left-sided sleep position for 10 minutes. The adapted threshold value will not exceed the initial threshold value. When being away from the left-sided sleep position for 40 minutes, the threshold value is adapted back to 30 minutes.

For example, an initial threshold value may be set at a 30 minutes duration for a non-movement in a left-sided sleep position. Now, before exceeding the 30 minutes, the user moves away to another position. The user moves away after 20 minutes which means that 10 minutes are left as a remaining duration regarding the left-sided sleep position. When being away from the left-sided sleep position for only 10 minutes, the threshold value will be adapted by 10 minutes. Because of the remaining duration, in this case the user is permitted to lay again in the left-sided sleep position for 20 minutes.

In an embodiment of the sleep position trainer, the non-movement of the user is detectable by the position sensor which is preferably an accelerometer. The position sensor is used to determine an actual sleep position and is used to determine whether or not the user remains in that actual sleep position.

In an embodiment of the sleep position trainer, the alert selector derived from the non-movement data determines a selection of an alert stimulus which differs from an alert stimulus which is selected in case of a detection of an occurrence of a sleep disturbing event, like laying in a supine position or an occurring apnoea. The selected alert stimulus may comprise a different intensity level or may be of another type, like an audible type or tactile type. The control unit is programmed to derive an alert selector from the non-movement data to determine a particular alert stimulus which differs from an alert stimulus provided to be generated in case of the sleep disturbing event. Herewith, a distinction is made in a manner of alerting for several sleep related events. Advantageously, an alert stimulus generated after a too long duration of non-movement differs from an alert stimulus generated after a sleep disturbing event which improves the training of the user.

In an embodiment of the sleep position trainer, the alert selector is derived from the non-movement data for a predetermined sleep phase. Herewith, an alert stimulus is to be generated based on the non-movement data for a predetermined sleep phase. Preferably, the selected alert stimulus is generated when the user is in a state of an arousal. A natural arousal may be awaited. When detecting the arousal by the sensor of the sleep position trainer, the selected alert stimulus may be generated to activate the user. A response may be detected by the sensor and a non-movement timer may be reset.

In an embodiment of the sleep position trainer according to the invention, the derived alert criterion and/or alert selector corresponds to a predetermined sleep phase. Advantageously, an alert stimulus may be generated in dependence of the predetermined sleep phase of the user. Herewith, a generated alert stimulus may be further tuned to a user specific needs. Preferably, no alert stimulus is generated in a last sleep phase of a sleep period to allow the user to awake without triggers, like vibrational stimuli, from the sleep position trainer.

According to a second aspect of the invention, the sleep position trainer comprises a memory for storing user sleep data which user sleep data contains personal sleep data of an individual user. Preferably, sensor data rendered by the at least one sensor is also stored on the memory. The sensor data is obtained by the at least one sensor during use of the sleep position trainer. The sensor data contains data of sleep related events. The user sleep data may be based on collected sensor data.

The control unit is programmed to derive an alert criterion from the user sleep data. The alert criterion is set based on the user sleep data stored in the memory. The alert criterion determines whether or not an alert stimulus is to be generated. The alert criterion determines whether or not the output signal is to be send to the alert unit.

Such a sleep position trainer may provide several advantages.

A first advantage is that the sleep position trainer according to the invention may be further optimised to a user specific needs. The operation of the sleep position trainer is tuned to a person's individual needs. The operation of the sleep position trainer is no longer based only on general programme rules which are valid to all users, but now the operation of the sleep position trainer is tailored to an individual user based on obtained user sleep data.

Based on retrieved or inputted user sleep data, the sleep position trainer can be set more or less strict to individual users. For example, from retrieved user sleep data during several sleep sessions, it may appear that a risk on an occurrence of a sleep affecting event, e.g. an occurrence of an apnoea, is low for a selection of the detected sleep related events. For example, the risk may appear to be low during an awakening sleep phase. Based on this user specific information, the alert criterion can be set less strict for this user during the awakening sleep phase. In this case, the derived alert criterion will be set to provide no alert signal for sleep related events which are detected during the last hour of the sleep period.

Other examples of deriving an alert criterion from the user sleep data are elaborated below in the described embodiments. Individually retrieved risk data, incidentally changing circumstances for an individual person, like a caught cold or a sleep period after an enjoyed party, a presence of a bed partner may all be user specific and defined in the user sleep data to set an alert criterion.

The user sleep data is stored in the memory of the apparatus. User sleep data is preferably stored on-board of the apparatus, such that the user sleep data is always directly available to the control unit of the sleep position trainer. User sleep data may be acquired by the at least one sensor during at least one sleep period of the user. During subsequent sleep periods of the user, already stored user sleep data may be adapted and updated. The sleep position trainer may be programmed to be self-learning such that the stored user sleep data remains always up to date. Alternatively, available user sleep data may be uploaded to the memory of the apparatus from an external data source, e.g. by a WiFi-connection.

The control unit is programmed to generate an output signal to the alert unit in dependence of the stored user sleep data. The output signal is preferably generated immediately after making a comparison of a received sensor signal and the alert criterion based on the stored personal user sleep data. A momentaneously occurring event during the users sleep which is detected by the sensor is compared with the alert criterion before sending an output signal to the alert unit. After receiving the output signal, the alert unit generates an alert stimulus. The alert stimulus corresponds to a desired stimulus which is associated with a certain person and sleep event. Herewith, the alert stimulus is tuned to a user needs. Advantageously, the sleep position trainer according to the invention may respond immediately in an appropriate manner to the user's sleep behaviour.

Another advantage of the sleep position trainer apparatus according to the invention is that the sleep position trainer may operate without any interference of the user self. The control unit is programmed with a control programme which is adapted to anticipate on user specifics. The control programme may include program rules or an algorithm. The control programme may be designed to anticipate on possible occurring sleep events. The possible occurring sleep events are pre-programmed sleep events. The control programme may prescribe selectable responses to these possible occurring sleep events. The user may fully rely on the control unit which is programmed to obtain an optimal operation for the individual user. No manually adapted settings may be necessary to be carried out by the user which increases user comfort. The increased user comfort contributes to an acceptance of the sleep position trainer which further contributes to a compliance of a sleep disorder treatment protocol.

In an embodiment of the sleep position trainer according to the invention, the sleep position trainer comprises a vibrator for generating a tactile stimulus. Advantageously, except for some buzzing sound, the vibrator allows to generate a non-audible stimulus for not disturbing a sleep of a bed partner of the user.

In an embodiment of the sleep position trainer according to the invention, the sleep position trainer is a wearable sleep position trainer and configured to be worn by the user. The sleep position trainer may include a neck or chest strap to attach the alert unit to a body part or a mouthpiece to attach the monitor and alert unit to a user's teeth.

In an embodiment of the sleep position trainer according to the invention, the alert unit is arranged to generate an alert stimulus which is selected from a group of alert stimuli. These selectable alert stimuli differ with respect to each other. The group of alert stimuli may represent a range of alert stimuli comprising alert stimuli within a range of a minimum and maximum alert stimulus.

In an embodiment of the sleep position trainer according to the invention, the control unit is programmed to derive an alert selector from the user sleep data. The alert selector determines a particular alert stimulus which is to be generated by the alert unit. The selection of an alert stimulus is made by the alert selector being programmed in the control programme of the control unit. The alert selector determines the output signal of the control unit. When receiving a particular output signal from the control unit, the alert unit provides a corresponding alert stimulus.

The alert selector is derived from the user sleep data which means that the alert selector is tuned to the user sleep data. The alert selector provides an output signal which determines an alert stimulus to be generated by the alert unit. The alert stimulus to be generated is selected by the alert selector which follows from the user sleep data. Particularly, the alert stimulus to be generated is a pre-set alert stimulus which is selectable by an alert selector derived from the user sleep data. The selectable alert stimuli differ with respect to each other, such that a less or more notable alert stimulus is available to alert the user. In particular, the alert stimuli differ in intensity with each other. Herewith, the sleep position trainer is arranged to respond in a different way to a detected sleep event for each individual user.

In an embodiment of the sleep position trainer according to the invention, the group of alert stimuli comprises at least three different alert stimuli. At least three different alert stimuli are selectable to be generated by the alert unit. The group of alert stimuli may include a low intensity stimulus, a medium intensity stimulus and a high intensity stimulus. Advantageously, a reaction of an individual user on an initial medium intensity stimulus can be detected by the sensor, whereafter the intensity of the stimulus can be adapted to a higher or lower intensity in case that the individual user has no satisfying response.

In an embodiment of the sleep position trainer according to the invention, the alert criterion is integral with the alert selector. The group of selectable alert stimuli comprises a zero-intensity alert stimulus. The zero-intensity alert stimulus will not be noted by a user. Herewith, the sleep position trainer may be programmed for a particular user to effectively ignore a detected sleep event by only deriving one alert parameter from the user sleep data.

In an embodiment of the sleep position trainer according to the invention, the memory for storing user sleep data is located at an external apparatus. The user sleep data may e.g. be stored in a memory of a smart phone. The user sleep data may be rendered by a smart phone application. The sleep position trainer is operatively connectable to the external apparatus to adapt the sleep position trainer by deriving the alert criterion and/or alert selector from the user sleep data which is stored in the external memory.

According to a third aspect of the invention, the user sleep data contains data of the individual user determining at least one sleep phase and corresponding risk data on an occurrence of a sleep disturbing event. Preferably, the risks data contains historic user sleep data representing detections of at least one, in particular at least two types of sleep events during a particular sleep phase. For each sleep phase, the user sleep data may include risk data which for example indicates how many apnoea's were earlier detected and how many snoring events were detected. An amount or intensity of these sleep events may be indicative of a particular risk on such sleep event during the sleep phase. The risk data may include at least two risk values indicating a risk within a range of a low to a high risk. Risk data may include two risk values indicating a low risk or a high risk. Risk data may include more than two risk values for also indicating an intermediate risk in between a low or high risk. Based on the risk data which is present for each sleep phase, the control unit is programmed to derive an alert criterion to determine whether or not an alert stimulus is to be generated and whether or not the output signal is to be sent to the alert unit.

Based on the risk data for each sleep phase, the control unit adapts the alert criterion. The alert criterion may for example indicate that no alert stimuli should be generated for snoring events during a particular sleep phase when the risk data at the same time indicates that no apnoea's were earlier detected during that particular sleep phase. Based on the risk data for each sleep phase, the control unit may adapt the alert selector. The working of the sleep position trainer may be mitigated which may contribute to a compliance to a sleep treatment protocol.

Advantageously, the sleep position trainer is customised as it is programmed for a particular user to respond user dependent during at least one sleep phase. After collecting initial sleep data of a particular user, an insight may be obtained that it is not necessary to alert the user during all sleep phases with the same intensity. Advantageously, in such a case, an outcome may be that a user needs not to be disturbed by an alert during a certain part of the sleep period. The memory may contain user sleep data which includes personal data including risk data which determines a desired alert stimulus for at least one sleep phase of the individual user. An insight may be obtained that a user should be alerted more intensive in a particular sleep phase or in contrast the user should be alerted less intensive in a particular sleep phase. According to the third aspect of the invention, the sleep position trainer is programmed to respond in correspondence with such an obtained insight.

In particular, the user sleep data defines a sleep period of the individual user which sleep period is subdivided into at least two sleep phases including corresponding risk data on an occurrence of a sleep disturbing event. Such a sleep disturbing event is for example a supine body posture, a snoring event or an occurrence of an apnoea. The risk data defines a probability of an occurrence of the sleep disturbing event. More in particular, the user sleep data defines a sleep period which is subdivided into successive sleep phases, wherein for each sleep phase a corresponding risk is determined. The user sleep data may contain risk data for all sleep phases and for a complete sleep period. Alternatively, the user sleep data may contain risk data for only a single sleep phase during a sleep period of a particular person.

Here, a sleep phase is a period of time within a defined sleep period. A sleep period has a starting point in which a person falls sleep and an end point in which a person is awake. The starting and/or end point of the sleep period may be detected by the sensor of the sleep position trainer. The sleep period may be subdivided into two or more sleep phases. The sleep period may be subdivided into constant time periods, e.g. each having a duration of half an hour. Alternatively, the sleep period may be subdivided into user dependent phases defining a time period of a deep or light sleep state. These sleep phases may vary in duration.

In an embodiment of the sleep position trainer, the risk data may contain user defined data. A user may input data for at least one sleep phase which is indicative for a particular risk on a sleep disturbing event. The user may set in a risk data that a particular sleep phase has a high, medium or low risk on a particular sleep disturbing event. The control unit is programmed to derive an alert criterion and/or alert selector from the set risk data.

In an embodiment of the sleep position trainer, the user sleep data may contain risk data which defines an allowance of a supine position for predetermined sleep phases. The user sleep data may for example define that a supine position of the user is permitted for at least one last sleep phases of a user sleep period, because a risk on a sleep disturbing event is low for those sleep phases. Advantageously, the sleep position trainer according to the invention does not generate an alert stimulus for all supine positions, but only for supine positions during a selected sleep phase which sleep phase brings a higher risk on a sleep disturbing event.

In an embodiment of the sleep position trainer according to the invention, the user sleep data of the sleep position trainer contains data of the individual user determining a sleep phase of a sleep period which has a higher risk on an occurring disturbing sleep event, which disturbing sleep event is an apnoea. Preferably, the sleep position trainer is programmed to generate a high intensive alert stimulus during this determined sleep phase when a sleep related event which might cause a disturbance is detected. The sleep position trainer embodied as a sleep position trainer is programmed to generate a high intensive alert stimulus during the determined sleep phase when a supine position is detected.

In an embodiment of the sleep position trainer according to the invention, the user sleep data of the sleep position trainer contains data of the individual user determining a sleep phase of a sleep period, a so-called awakening sleep phase, in which the user wakes up. Typically, such awakening sleep phase differs for several users. For some users, the awakening sleep phase has a relative long duration of about half an hour and for others the awakening sleep phase is relatively short. Preferably, the user sleep data is historic user sleep data obtained by detections in previous uses of the sleep position trainer. The user sleep data contains risk data on a presence of a sleep disturbing event during the awakening sleep phase. Generally, most users will have a low risk on a sleep disturbing event during the awakening sleep phase.

Advantageously, the sleep position trainer takes care of different durations and exceptions differing from a general situation. Herewith, the sleep position trainer responds more accurate to individual users because the risk data is user dependent and may for some individuals prescribe that a more intensive alert stimulus needs to be generated during the awakening sleep phase.

According to a fourth aspect of the invention, the sleep position trainer apparatus further comprises an await timer and await data determining a permitted waiting-time period before generating an alert stimulus. The await timer is provided to limit a possible delay in generating an alert stimulus in response to a detected sleep event. During a sleep period, a detection of a sleep event may activate the await timer when the alert criterion determined that no alert stimulus is to generated or when after a generated alert stimulus no adequate response of the user is detected. The await timer is provided to limit e.g. a waiting time for an occurrence of an arousal of the user, a duration of snoring, a period of no adequate response. During the permitted waiting-time period, subsequent alert stimuli if no adequate response is detected may be cancelled. The await timer may prevent a too early generation of a subsequent alert stimulus which may mitigate a sleep training.

In an embodiment of the sleep position trainer, the users sleep data contains await data of the individual user determining an acceptable waiting-time period before generating an alert stimulus. In particular, the waiting-time period determines a permitted time period for awaiting a predetermined sleep phase. A set value of a permitted waiting-time period may prevent a too long duration of e.g. a non-movement of the user or a supine position of a user in awaiting a predetermined sleep phase.

According to a fifth aspect of the invention, the user sleep data contains snoring data of an individual user. The control unit is programmed to derive the alert criterion and/or alert selector from the snoring data to generate the output signal to the alert unit. A risk on an occurrence of a sleep disturbing event may relate to a snoring event, but such a risk may differ for several users. By setting the user sleep data for each individual user, a response of the sleep position trainer to a detection of a snoring event may differ. A user may receive a first alert stimulus, while a another user receives another alert stimulus when a snoring event is detected.

In an embodiment of the sleep position trainer, the snoring data determines a selection of an alert stimulus which differs from an alert stimulus which is selected in case of a detection of an occurrence of a sleep disturbing event, like laying in a supine position or an occurring apnoea. The control unit is programmed to derive an alert selector from the snoring data to determine a particular alert stimulus which differs from an alert stimulus provided to be generated in case of the sleep disturbing event. Advantageously, an alert stimulus generated after a snoring event differs from an alert stimulus generated after a sleep disturbing event which improves a training of the user.

According to a sixth aspect of the invention, the user sleep data contains prediction data of an individual user determining an expected sleep quality, also called a sleep quality forecast. The control unit is programmed to derive an alert criterion from the prediction data to determine whether or not alert stimulus is to be generated. The control unit may be programmed to derive an alert selector from the prediction data to determine a particular alert stimulus which is to be generated by the alert unit. Based on the prediction data, a particular alert stimulus is selected when a sleep related event is detected during use. Particularly, the prediction data determines a particular intensity of an alert stimulus. When a restless sleep is predicted and indicated by the prediction data of the user sleep data, the sleep position trainer may trigger the user at a less intensive level. By adapting the alert stimulus in dependence of the prediction data, the user may enjoy an improved sleep quality which is less disturbed by the operation of the sleep position trainer. The user is alerted by an alert stimulus which is dedicated to occurring circumstances. The prediction data contributes to an improved comfort of the sleep position trainer which improves a compliance to a sleep treatment protocol.

In an embodiment of the sleep position trainer, the user may manually input prediction data of an expected sleep quality into the sleep position trainer. The sleep position trainer may provide a menu to the user which menu may allow the user to select a prediction parameter of the user sleep data. The user may select a prediction which indicates an expected good, moderate or restless sleep. The user may e.g. expect a good sleep based on an experience that the user normally sleeps well after a day spending some hours outdoors. The prediction parameter indicating an expected good sleep may determine a high intensive alert stimulus. To the contrary, a user may e.g. expect a restless sleep after a stressful day. The prediction data indicating a restless sleep may result in a low intensive alert stimulus to prevent too much disturbance of a sleep of the user by the sleep position trainer.

In an embodiment of the sleep position trainer, the prediction data is stored in a memory external from the sleep position trainer apparatus. The prediction data may for example be stored in a memory of a smart phone. The user may input a prediction in an application of a smart phone. The external memory is operatively connectable with the sleep position trainer. The control unit may communicate with the external memory for deriving the alert criterion and/or alert selector.

In an embodiment of the sleep position trainer, the prediction data may be adapted based on measurements carried out during a period before going to sleep. In particular, the measurements may be carried out by a personal health device. Preferably, the personal health device is a portable personal health device, like a sport watch. The personal health device may for example be a separate heart rate measurement device which measures a heart rate during a certain period of time. The personal health device comprises a memory for storing user data which memory may be operatively connectable to the sleep position trainer to communicate with the sleep position trainer. Alternatively, the personal health device may be incorporated with the sleep position trainer. A logged heart rate measurement may set a prediction data of the user sleep data of the sleep position trainer to indicate an expected quality of sleep, e.g. a good moderate or restless sleep.

According to a seventh aspect of the invention, the user sleep data contains bed partner data determining whether or not a bed partner is present. The control unit is programmed to derive an alert criterion from the bed partner data to determine whether or not an alert stimulus is to be generated. A presence of a bed partner may determine that only for a part of the sleep events an alert stimulus is to be generated. The control unit may be programmed to derive an alert selector from the bed partner data to determine a particular alert stimulus which is to be generated by the alert unit. A presence of a bed partner determines a selection of an alert stimulus to be generated. A particular, e.g. noisy, alert may disturb a sleep of a bed partner. When a bed partner is present, the user sleep data may indicate this and the sleep position trainer may respond different in comparison with a situation in which no bed partner is present. The sleep position trainer may respond for several sleep related events. In case that a bed partner is present, the sleep position trainer may respond for more or less sleep related events in comparison with a situation in which no bed partner is present. In case that a bed partner is present, the control unit may e.g. be programmed to generate an output signal to the alert unit to generate an alert stimulus to the user in case of a detected sleep related event, e.g. a snoring event, while no alert stimulus would be generated in case that no bed partner is present. Such a snoring event may disturb a sleep of a bed partner, but might not be disturbing for the user self. For that reason, it is advantageous that the sleep position trainer is adaptive to different situations. The sleep position trainer responds in a different manner for situations in which a bed partner is present or in which no bed partner is present. The sleep position trainer may e.g. be programmed to generate a tactile alert stimulus instead of an audible alert stimulus in case that a bed partner is present. The sleep position trainer may be programmed to generate a more moderate alert stimulus in case that a bed partner is present. Advantageously, the sleep position trainer has an optimised working under distinguishing circumstances.

In an embodiment of the sleep position trainer, the sleep position trainer apparatus may further comprise a bed partner device. The bed partner device is arranged to be worn by the bed partner of the user of the sleep position trainer. The bed partner device may include a device strap for attaching the bed partner device to a body part of the bed partner. The bed partner device may for example be attached to an arm or a wrist of the bed partner.

In an embodiment of the sleep position trainer, the bed partner device comprises a device sensor for detecting a sleep state of the bed partner. The device sensor may be arranged for detecting whether the bed partner is awake or asleep. The device sensor may be arranged for detecting a sleep state, like a deep sleep, light sleep, arousal of the bed partner. The device sensor is e.g. accelerometer for detecting movements of the bedpartner or a microphone for measuring a respiration of a person.

The control unit of the sleep position trainer is programmed to generate the output signal to the alert unit based on a received bed partner signal which bed partner signal corresponds to a detected sleep state of the bed partner. When the bed partner experiences an arousal, it may be better not to alert the user of sleep position trainer to prevent a sleep disturbance of the bed partner. It may be better to await generating the alert stimulus until the arousal of the bed partner is over. Advantageously, the sleep position trainer does not harm a sleep quality of a bed partner of the user. The combination of the sleep position trainer and the bed partner device may increase an acceptancy level of the sleep position trainer. Advantageously, the bed partner device contributes to an increase in compliance to a sleep treatment protocol of the user of the sleep position trainer.

Further, the invention relates to a bed partner device. The bed partner device is arranged to be worn by a bed partner of a user of a sleep position trainer apparatus. The bed partner device comprises a device control unit including a device control programme which is programmed to generate a device output signal based on at least one received device input signal;

at least one device sensor for detecting a sleep related event, which sensor is operatively connected to the device control unit to provide a device sensor signal to the device control unit; a device transmitter for transmitting the device output signal, also called a bed partner signal to the sleep position trainer of the user; and the sleep position trainer comprises a receiver for receiving the bed partner signal, wherein the control unit of the sleep position trainer is programmed to control the sleep position trainer based on the received bed partner signal.

In an embodiment of the sleep position trainer according to the invention, the control unit is programmed with a dominant program to overrule all other programs in case that the sensor detects a high risk sleep event, e.g. an apnoea. The control programme of the control unit may include programs which deal with the sleep phase data, prediction data, snoring data, non-movement data, bed partner data as described above to generate a dedicated alert stimulus. The dominant program prevents an undesired omitting of an alert stimulus in case of a high risk sleep event.

Further embodiments according to aspects of the invention are defined in the following clauses with reference to appended drawings in parenthesis:

1. Sleep position trainer apparatus (1) for improving a sleep quality of a user comprising:
   a control unit (CU) which control unit includes a control programme which is programmed to generate an output signal based on at least one received input signal;
   at least one sensor (S) for detecting a sleep related event, which sensor is operatively connected to the control unit to provide a sensor signal as a first input signal to the control unit;
   an alert unit (AU) for providing an alert stimulus to the user wearing the sleep position trainer apparatus, which alert unit is operatively connected to the control unit to receive the generated output signal from the control unit, whereafter the alert stimulus is provided;
   a memory (M) for storing user sleep data (USD) which user sleep data contains personal sleep data of an individual user,
   wherein the control unit (CU) is programmed to derive an alert criterion (c1) from the user sleep data to determine whether or not an alert stimulus is to be generated and whether or not the output signal is to be send to the alert unit.

2. Sleep position trainer according to clause 1, wherein the control unit (CU) is programmed to derive an alert selector (s1) from the user sleep data (USD) to determine a particular alert stimulus which is to be generated by the alert unit which alert stimulus is selected from a group of alert stimuli (f1, f2) which alert stimuli differ with respect to each other.

3. Sleep position trainer according to claim 2, wherein the alert criterion (c1) is integral with the alert selector (s1), wherein one of the selectable alert stimulus has a zero-intensity.

4. Sleep position trainer according to any of the preceding clauses, wherein the memory for storing user sleep data is located at an external apparatus, e.g. a smart phone, wherein the external apparatus is operatively connectable to the sleep position trainer apparatus to adapt the sleep position trainer by deriving the alert criterion (c1) and/or alert selector (s1) from the externally stored user sleep data.

5. Sleep position trainer according to any of the clauses 1-4, wherein the user sleep data contains prediction data of an individual user which prediction data determines an expected sleep quality, wherein the control unit is programmed to derive the alert criterion and/or alert selector from the prediction data to generate the output signal to the alert unit.

6. Sleep position trainer according to any of the preceding clauses, wherein the user sleep data contains bed partner data of the individual user determining whether or not a bed partner is present.

7. Sleep position trainer according to clause 6, wherein in case that a bed partner is present, the control unit is programmed to generate an output signal to the alert unit to generate an alert stimulus to the user in case of a detected sleep related event, in particular a snoring event, while in case that no bed partner is present said alert stimulus is not generated in response to said sleep related event.

8. Sleep position trainer according to clause 6 or 7, wherein the control unit is programmed to generate an output signal to the alert unit to generate an alert stimulus to the user in case of a detected sleep related event and a presence of a bed partner, which alert stimulus is a moderate alert stimulus in comparison with an alert stimulus to be generated in case that no bed partner is present.

9. Sleep position trainer according to any of the clauses 6-8, wherein the sleep position trainer further comprises a bed partner device, wherein the bed partner device is arranged to be worn by the bed partner, wherein the bed partner device comprises:
  a device control unit including a device control programme which is programmed to generate a device output signal based on at least one received device input signal; and
  at least one device sensor for detecting a sleep related event, which sensor is operatively connected to the device control unit to provide a device sensor signal to the device control unit;
  a device transmitter for transmitting the device output signal, also called a bed partner signal to the sleep position trainer of the user;
wherein the sleep position trainer comprises a receiver for receiving the bed partner signal, wherein the control unit of the sleep position trainer is programmed to control the sleep position trainer based on the received bed partner signal.

10. Sleep position trainer according to clause 9, wherein the bed partner device comprises a device sensor for detecting a sleep state of the bed partner, wherein the control unit of the sleep position trainer is programmed to generate the output signal based on a received bed partner signal corresponding to a detected sleep state of the bed partner.

11. Bed partner device which is arranged to be worn by a bed partner of a user of a sleep position trainer apparatus, wherein the bed partner device comprises:
  a device control unit including a device control programme which is programmed to generate a device output signal based on at least one received device input signal; and
  at least one device sensor for detecting a sleep related event, which sensor is operatively connected to the device control unit to provide a device sensor signal to the device control unit;
  a device transmitter for transmitting the device output signal, also called a bed partner signal to the sleep position trainer of the user;
wherein the sleep position trainer comprises a receiver for receiving the bed partner signal, wherein the control unit of the sleep position trainer is programmed to control the sleep position trainer based on the received bed partner signal.

12. Sleep position trainer apparatus (1) for improving a sleep quality of a user comprising:
  a control unit (CU) which control unit includes a control programme which is programmed to generate an output signal based on at least one received input signal;
  at least one sensor (5) for detecting a sleep related event, which sensor is operatively connected to the control unit to provide a sensor signal as a first input signal to the control unit, wherein the sleep position trainer is a sleep position trainer, which sleep position trainer comprises a position sensor (34) for detecting a body posture of a person wearing the sleep position trainer;
  an alert unit (AU) for providing an alert stimulus to the user wearing the sleep position trainer apparatus, which alert unit is operatively connected to the control unit to receive the generated output signal from the control unit, whereafter the alert stimulus is generated; wherein the sleep position trainer has a normal operational mode for alerting during a user's sleep period, in which normal operational mode the control unit generates an output signal to the alert unit, and the alert unit generates an alert stimulus when a posture of the body detected by the position sensor (34) corresponds with at least one predefined undesired body posture, wherein the sleep position trainer further comprises a non-movement timer (t1) for timing a non-movement period of the user wearing the sleep position trainer, wherein the control unit (CU) is programmed to send an output signal to the alert unit in case that a posture of the body detected by the position sensor (34) corresponds with a body posture other than the at least one predefined undesired posture when a threshold value of the non-movement timer (t1) of at least 15 minutes is exceeded.

13. Sleep position trainer according to clause 12, wherein the threshold value is a predetermined threshold value.

14. Sleep position trainer according to clause 12, wherein the sleep position trainer apparatus further comprises:
  a memory (M) for storing user sleep data (USD) which user sleep data contains personal sleep data of an individual user,
wherein the control unit (CU) is programmed to derive an alert criterion (c1) from the user sleep data to determine whether or not an alert stimulus is to be generated and whether or not the output signal is to be send to the alert unit, wherein the user sleep data contains non-movement data of the individual user including at least one threshold value indicating a duration of a non-movement period of the user in a certain posture other than the at least one predefined undesired posture during a sleep period.

15. Sleep position trainer according to clause 14, wherein the non-movement data includes at least one threshold value corresponding with at least one posture of the user.

16. Sleep position trainer according to clause 14 or 15, wherein the non-movement data includes at least one threshold value corresponding with at least one predetermined sleep phase of the user.

17. Sleep position trainer according to any of the preceding clauses, wherein the at least one threshold value of the non-movement timer (t1) is adaptable in dependence of a particular response on a generated stimulus caused by an excess of a previous threshold value.

18. Sleep position trainer according to clause 17, wherein the threshold value of the non-movement timer for a certain posture is adaptable based on measured earlier durations in said certain posture during a same sleep period.

19. Sleep position trainer according to clause 17 or 18, wherein an initial threshold value of the non-movement timer (t1$i$) is initially set for a certain posture and adaptable based on a timed duration of being away from said certain posture.

20. Sleep position trainer according to clause 19, wherein the initial threshold value is adapted by a duration which is either equal to the timed duration of being away from said certain posture or adapted by a reset to the initial set threshold value in case that said duration of being away from said certain posture exceeds the initial threshold value.

21. Sleep position trainer according to any of the preceding clauses, wherein non-movement of the user is detectable by the position sensor (34), in particular an accelerometer.

22. Sleep position trainer according to any of the preceding clauses, wherein the control unit (CU) is programmed to derive an alert selector (s1) from the user sleep data (USD) to determine a particular alert stimulus which is to be generated by the alert unit which alert stimulus is selected from a group of alert stimuli (f1, f2) which alert stimuli differ with respect to each other.

23. Sleep position trainer according to any of the preceding clauses, wherein the alert criterion (c1) is integral with the alert selector (s1), wherein one of the selectable alert stimulus has a zero-intensity.

24. Sleep position trainer according to clause 22 or 23, wherein the alert selector (s1) derived from the non-movement data determines a selection of an alert stimulus which differs from an alert stimulus to be generated in case of a detection of an occurrence of a sleep disturbing event.

25. Sleep position trainer according to any of the preceding clauses, wherein the memory for storing user sleep data is located at an external apparatus, e.g. a smart phone, wherein the external apparatus is operatively connectable to the sleep position trainer apparatus to adapt the sleep position trainer by deriving the alert criterion (c1) and/or alert selector (s1) from the stored user sleep data.

26. Sleep position trainer according to any of the preceding clauses, wherein the control unit is programmed with a dominant program to overrule all other programs in case that the sensor detects a high risk on a sleep event, e.g. an apnoea.

27. Sleep position trainer according to any of the preceding clauses, wherein the user sleep data contains await data determining an acceptable waiting-time period before generating an alert stimulus.

28. Method for alerting a person during a sleep period comprising the steps of:
 providing a sleep position trainer apparatus according to any of the preceding clauses, wherein the sleep position trainer apparatus is a sleep position trainer including a position sensor (34) for detecting a posture of the user;
 detecting a sleep position of the user during its sleep;
 alerting the user in case that a predefined undesired posture, in particular a supine position, is detected;
 timing a duration of non-movement of the user during its sleep by a non-movement timer of the sleep position trainer apparatus;
 comparing a timed duration of a non-movement with a threshold value;
 alerting the user in case that at least one other posture than the at least one predefined undesired posture is detected and the timed duration of a non-movement exceeds the threshold value of at least 15 minutes.

29. Sleep position trainer apparatus (1) for improving a sleep quality of a user comprising:
 a control unit (CU) which control unit includes a control programme which is programmed to generate an output signal based on at least one received input signal;
 at least one sensor (5) for detecting a sleep related event, which sensor is operatively connected to the control unit to provide a sensor signal as a first input signal to the control unit, wherein in particular a detection of the at least one sensor (S) is stored as sensor data;
 an alert unit (AU) for providing an alert stimulus to the user wearing the sleep position trainer apparatus, which alert unit is operatively connected to the control unit to receive the generated output signal from the control unit, whereafter the alert stimulus is provided;
 a memory (M) for storing user sleep data (USD) which user sleep data contains personal sleep data of an individual user,
wherein the control unit (CU) is programmed to derive an alert criterion (c1) from the user sleep data to determine whether or not an alert stimulus is to be generated and whether or not the output signal is to be send to the alert unit, wherein the user sleep data contains sleep phase data of the individual user determining at least one sleep phase and corresponding risk data on an occurrence of a sleep disturbing event.

30. Sleep position trainer according to clause 29, wherein the control unit (CU) is programmed to derive an alert selector (s1) from the user sleep data (USD) to determine a particular alert stimulus which is to be generated by the alert unit which alert stimulus is selected from a group of alert stimuli (f1, f2) which alert stimuli differ with respect to each other.

31. Sleep position trainer according to clause 30, wherein the alert criterion (c1) is integral with the alert selector (s1), wherein one of the selectable alert stimulus has a zero-intensity.

32. Sleep position trainer according to any of the preceding clauses, wherein the memory for storing user sleep data is located at an external apparatus, e.g. a smart phone, wherein the external apparatus is operatively connectable to the sleep position trainer apparatus to adapt the sleep position trainer by deriving the alert criterion (c1) and/or alert selector (s1) from the stored user sleep data.

33. Sleep position trainer according to clause 32, wherein the user sleep data contains risk data which is user defined risk data.

34. Sleep position trainer according to clause 32, wherein the risk data contains historic user sleep data, in particular including collected sensor data, representing detections of at least one type of sleep events during a particular sleep phase, wherein the control unit is programmed to derive an alert criterion and/or alert selector from the risk data for a particular sleep phase.

35. Sleep position trainer according to any of the preceding clauses, wherein the risk data defines an allowance of a supine position for at least one predetermined sleep phase.

36. Sleep position trainer according to clause 35, wherein the predetermined sleep phase is an awakening sleep phase.

37. Sleep position trainer according to any of the preceding clauses, wherein the risk data contains user sleep data representing detections of at least two types of sleep events during a particular sleep phase, wherein the control unit is programmed to derive an alert criterion and/or alert selector from the risk data for a particular sleep phase in which the at least two types of sleep events are balanced.

38. Sleep position trainer apparatus according any of the preceding clauses, wherein the user sleep data contains risk data determining a sleep phase of a sleep period which has a higher risk on an occurrence of an apnoea.

39. Sleep position trainer according to any of the preceding clauses, wherein the sleep position trainer comprises an await timer and await data determining a permitted waiting-time period before generating an alert stimulus.

40. Sleep position trainer according to clause 39, wherein the user sleep data contains await data determining a permittable waiting-time period before generating an alert stimulus.

41. Sleep position trainer according to any of the preceding clauses, wherein the user sleep data contains snoring data of the individual user, wherein the control unit is programmed to derive the alert criterion and/or alert selector from the snoring data to generate the output signal to the alert unit.

42. Sleep position trainer according to clause 41, wherein the alert selector derived from the snoring data determines a selection of an alert stimulus which differs from an alert stimulus to be generated in case of a detection of an occurrence of another sleep disturbing event, in particular an occurrence of an apnoea.

The invention will be explained in more detail with reference to the appended drawings. The drawings show a practical embodiment according to the invention, which may not be interpreted as limiting the scope of the invention. Specific features may also be considered apart from the shown embodiment and may be taken into account in a broader context as a delimiting feature, not only for the shown embodiment but as a common feature for all embodiments falling within the scope of the appended claims, in which:

Figure 1:
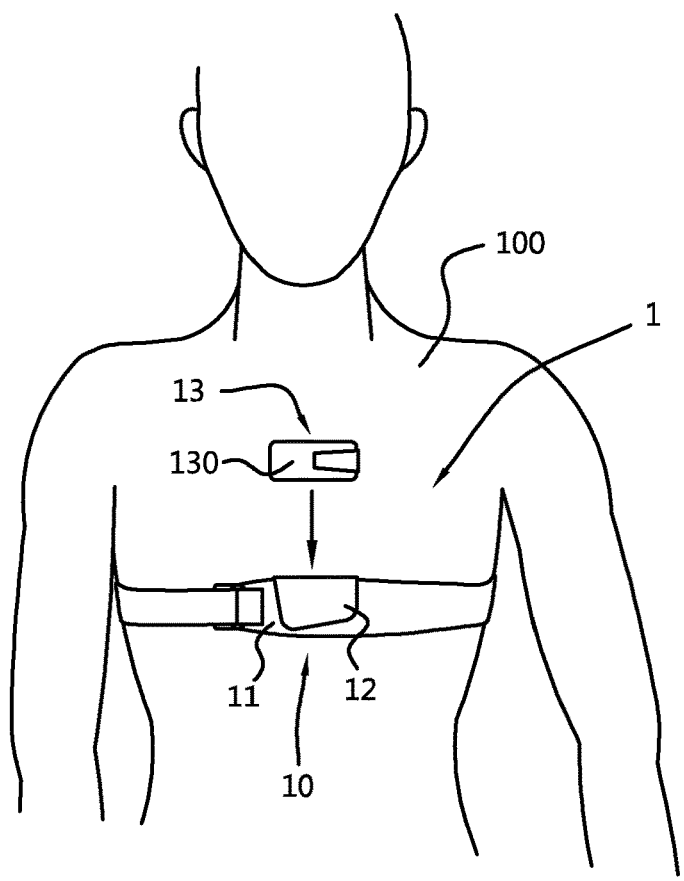
FIG. 1 shows a frontal view of a user wearing a sleep position trainer apparatus according to the invention.

Identical reference signs are used in the drawings to indicate identical or functionally similar components.

FIG. 1 shows in a frontal view a sleep position trainer 1 which is worn by a user 100 lying on a bed 101. The sleep position trainer 1 is arranged for improving a sleep quality of a person. Here, the sleep position trainer 10 is configured for training a user 100 to avoid an undesired posture, e.g. a supine or prone position, during a sleep period. The sleep position trainer 10 trains the user to sleep in a posture which has a low risk on a sleep disturbing event.

The sleep position trainer is a wearable sleep position trainer. Here, the sleep position trainer comprises a monitor 13 and a strap 11 for attaching the monitor 13 to a user's body. The monitor 13 is releasable and for use received inside a pocket 12 of the strap 11. The strap 11 is attached to an upper body of the user 100. Here, the strap 11 is positioned around the chest. Alternatively, the strap 11 may be worn around the neck, waist or other position of the upper body.

The monitor 13 is arranged for receiving and processing a signal from at least one sensor, in particular a position sensor. The monitor 13 includes a monitor housing 130 for housing electronic components, like a control unit CU, memory M, battery etc. The monitor housing 130 is made of a plastic material by injection moulding.

Figure 2:
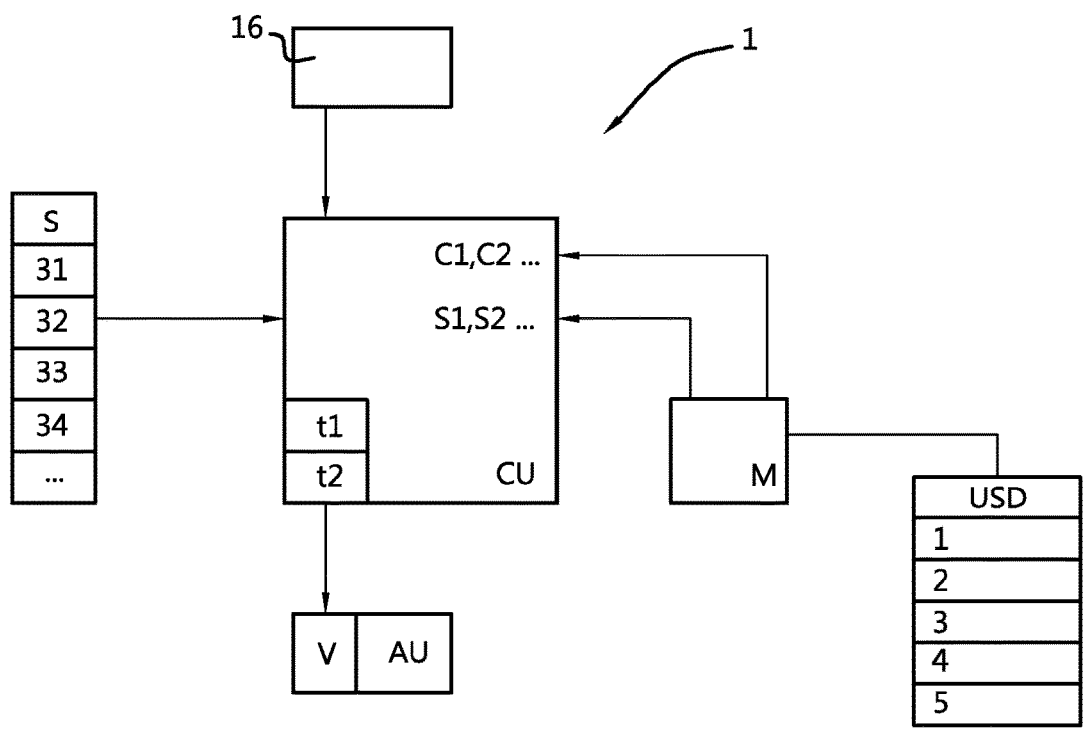
FIG. 2 shows a schematic view of electronic components of a sleep position trainer.

FIG. 2 shows in a schematic view the sleep position trainer 1 in further detail. Several cooperating electronic components are indicated.

The sleep position trainer 1 comprises a control unit CU. The control unit comprises a control programme. The control programme is programmed to generate an output signal based on at least one received input signal.

The sleep position trainer 1 comprises at least one sensor S for detecting a sleep related event. An example of such a sensor is a heart rate sensor 33, respiration sensor, temperature sensor 31, microphone 32, position sensor 34, accelerometer etc. Such a sensor is arranged to detect a sleep related event, like a sleep posture, sleep temperature, snoring, movement, sleep sound, sleep respiration etc.

The sleep position trainer 1 comprises at least one alert unit AU for providing an alert stimulus to the user wearing the sleep position trainer. The alert unit may comprise a speaker to generate an audible alert stimulus. Preferably, the alert unit comprises a vibrator V to provide a tactile alert stimulus. The alert unit is operatively connected to the control unit CU to receive the generated output signal from the control unit. In response to a received signal, the alert unit provides an alert stimulus.

A sleep position trainer 1 including a position sensor for detecting a posture of a user can be used as a sleep position trainer to alert a person wearing the sleep position trainer in an event that the person is in a predetermined undesired position. The position sensor may be arranged to detect an upright position or a lying position of the person. Preferably, the position sensor is arranged to detect a predetermined orientation in a lying position. The predetermined orientation is for example a supine, a prone, a left-sided, a right-sided or other position oriented with respect to a sagittal plane. Preferably, such a sleep position trainer comprises a vibrator to allow a tactile stimulus to stimulate a person to change position during a sleep period.

The sleep position trainer 1 comprises a memory M for storing user sleep data USD which user sleep data contains personal sleep data of an individual user. The user sleep data contains data of an individual user relating to a sleep related event.

The user sleep data may contain non-movement data USD1, sleep phase data USD2, risk data USD3, prediction data USD4, bed partner data USD5 as described above. Preferably, the user sleep data is collected by the sleep position trainer 1 and contains sensor data.

The control unit CU is programmed to derive an alert criterion c1 from the user sleep data USD to determine whether or not an alert stimulus is to be generated and whether or not to send the output signal to the alert unit.

Further, the control unit CU is programmed to derive an alert selector s1 from the user sleep data USD to determine a particular alert stimulus which is to be generated by the alert unit. The alert selector s1 determines which alert stimulus is selected from a group of different alert stimuli.

When receiving an input signal from the at least one sensor S, the control unit CU may generate an output signal or an output signal may not be generated which depends on a compliance to the alert criterion c1. The alert criterion c1 is derived from the user sleep data which is stored in the memory M. The alert criterion c1 is set in accordance with user sleep data USD. As the user sleep data is dedicated to a particular individual person, the alert criterion c1 is a user dependent criterion. For each user, a particular alert criterion c1 is derived.

The user sleep data may contain sleep phase data in which a sleep phase is defined together with risk data indicating a risk on an occurrence of a sleep disturbing event. Based on the sleep phase data, the derived alert criterion c1 may determine for each defined sleep phase whether or not an output signal is to be generated.

The risk data may be general risk data which is universal to all users. When a user enters a predetermined sleep phase, the risk data determines the alert criterion to determine whether or not in that sleep phase and alert stimulus should be generated. The risk data may for example determine that no stimulus should be generated when the sleep phase is an awakening sleep phase. Preferably, the risk data further determines an alert selector s1 for a selection of an alert stimulus.

The risk data may be defined by an analysis of collected sleep data of a user. The risk data may be defined by a doctor or sleep coach who is assisting the user in a sleep therapy. Preferably, the control programme of the control unit comprises an algorithm to analyse collected sensor data to produce risk data per sleep phase. Advantageously, the risk data obtained by collected sensor data is tuned to a specific user. Herewith, the sleep position trainer is further customised.

Preferably, the analysis is performed on collected sleep data of the user regarding a plurality of sleep periods. The sleep data may contain data of at least five sleep periods, in particular at least fifteen sleep periods which represents some weeks of sleep therapy. The analysis of the sleep data may have an outcome in that in some sleep phases, no sleep disturbing events, like snoring or an apnoea, are detected while at the same time other sleep related events, like an increase in heart rate or respiration rate, are present and should normally induce a stimulus. In that case, the risk for that sleep phase may be set at a low level. Based on the indicated low-level, a mitigated alert stimulus may be selected and generated by the sleep position trainer during the corresponding sleep phase.

The analysis of the sleep data may have another outcome in that in a particular sleep phase, a risk on a sleep disturbing event is high. Consequently, the user sleep data may contain risk data which indicates for that particular sleep phase a high risk. Based on the indicated high risk, a strong alert stimulus may be selected and generated by the sleep position trainer during the corresponding sleep phase.

The control unit CU comprises a internal clock. The internal clock can be used to timestamp and register an event in the memory M. The control unit may comprises at least one timer t for timing a duration of a sleep event. The control unit may comprise a non-movement timer t1 or an await timer t2 for timing respectively a duration of a non-movement or an elapsed time since an occurrence of a sleep event.

Figure 3A:
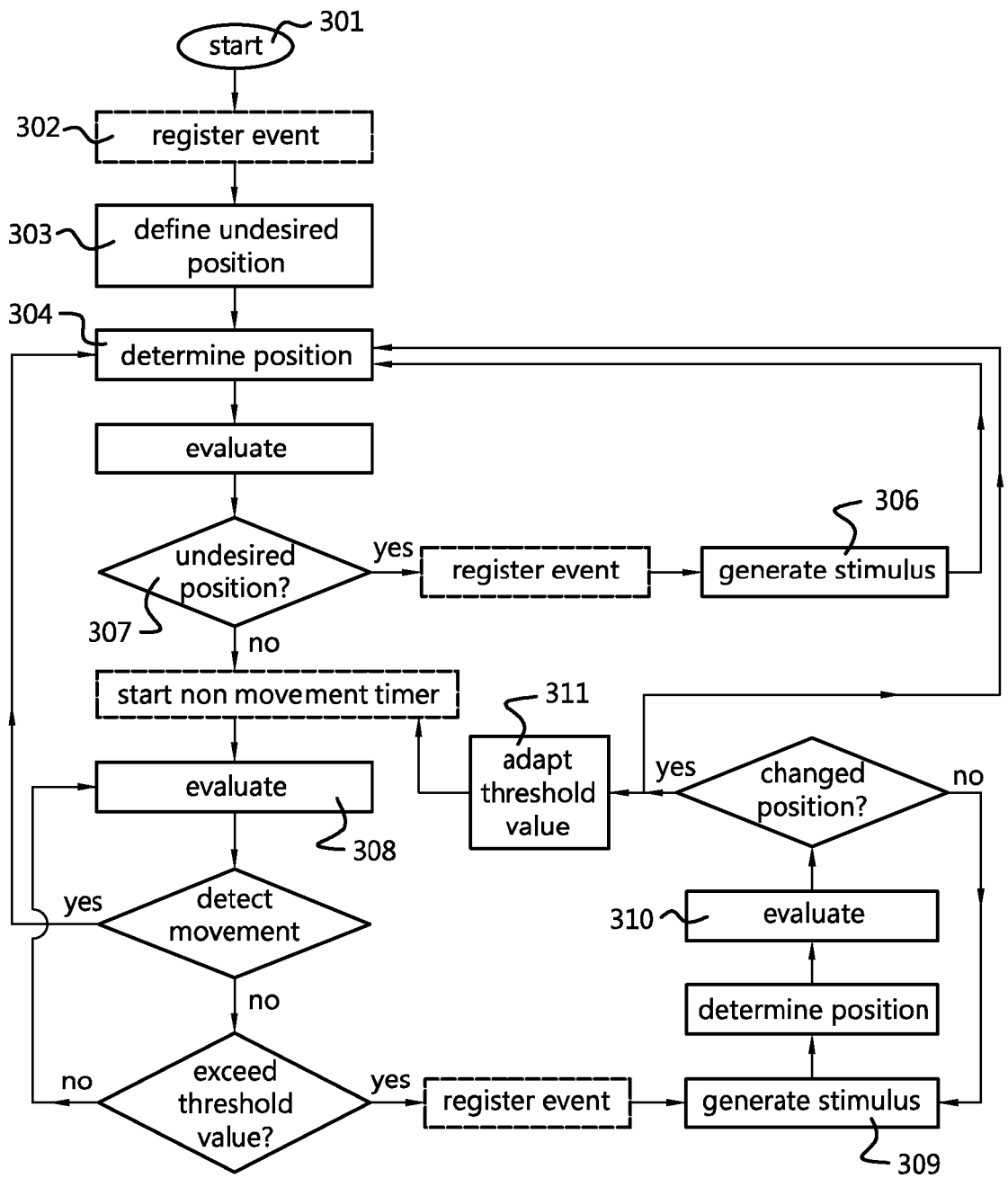
FIG. 3A shows a flow scheme of operational steps of a sleep position trainer including steps for observing and acting on non-movement in a certain sleep position.

FIG. 3A shows a flow scheme of a normal operation of the sleep position trainer apparatus including a non-movement timer t1 to prevent a too long duration of non-movement of a user in a certain sleep position.

The flow scheme has a first step 301 in which the sleep position trainer apparatus is started. The sleep position trainer apparatus may have a start button which allows the user to manually activate the sleep position trainer. Preferably, the sleep position trainer apparatus includes an automatic start feature, e.g. provided by a temperature sensor which on detection of a body temperature starts the apparatus. Advantageously, such automatic start feature further minimises a user interference in use of the sleep position trainer. Typically, an event 302 is registered when starting the sleep position trainer.

The sleep position trainer is a sleep position trainer which is arranged to detect a sleep position, or also called a sleep posture, of a user. At least one undesired sleep position is predefined 303 for a sleep period. Preferably, a supine position is predefined as an undesired position during a sleep period of a user. Particularly, at least one predefined undesired sleep position is programmed in a control programme of a control unit of the sleep position trainer. During operation a position of the user is detected and determined 304 by the position sensor 34. First, an evaluation 305 is made whether or not the determined position is an undesired position. If it is determined that the user is in the undesired position, this event is registered and a stimulus 306 is generated to stimulate the user to change position.

If it is determined that the user is in another position than the at least one predefined undesired position, the non-movement timer t1 is started 307. A duration of non-movement is evaluated 308. In the evaluation 308, it is evaluated whether or not a state of non-movement is still present. A detection of a movement of the user from a certain posture to another posture resets the non-movement timer t1 and restarts the operational steps 304. This event may be registered including a registration of a duration of non-movement in the certain posture for future purposes. The registration of the duration may be entered in the sensor data. In the evaluation 308, a comparison is made with a threshold value to prevent a too long duration of non-movement in a same position. Typically, the evaluation 308 is carried out in a programmed frequency of e.g. 1 Hz.

If it is determined that the duration of non-movement exceeds a threshold value, a registration of this event is made and a stimulus is generated to stimulate the user to change position. After generating the stimulus, a position of the user is determined by the position sensor 34 and evaluated 310 to determine a positional change. If no positional change has occurred, the user is stimulated again. If a positional change has occurred, the non-movement timer t1 is reset and the cycle 304-310 is restarted.

The flow scheme further shows a further embodiment including a step of an adaption of the threshold value 311 of the non-movement timer t1. Once a first maximum duration for a certain sleep position which maximum duration is determined by exceeding an initial threshold value t1$i$, the threshold value is adapted.

Figure 3B:
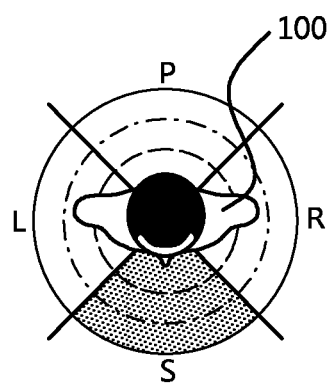
FIG. 3B shows in a schematic view a method of balancing durations of non-movement in certain sleep positions with respect to each other.
Figure 3B:
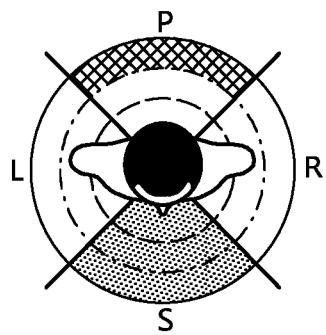
Figure 3B:
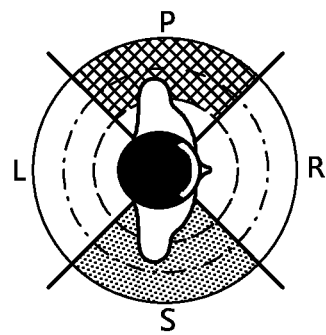
Figure 3B:
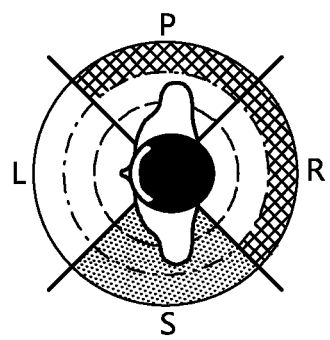
Figure 3B:
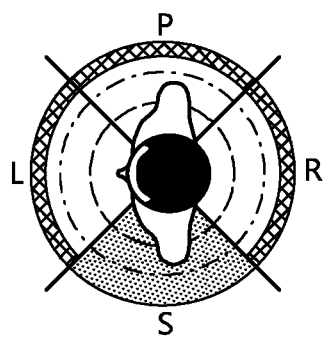
Figure 3B:
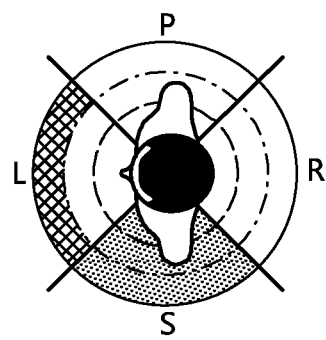
Figure 3B:
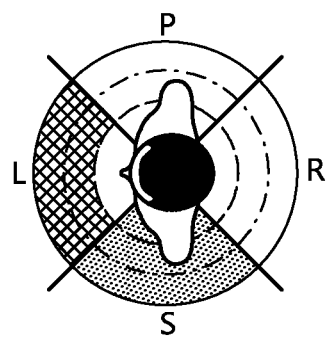
Figure 3B:
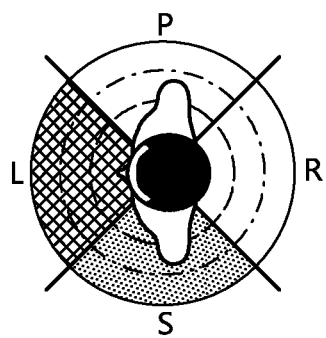
Figure 3B:
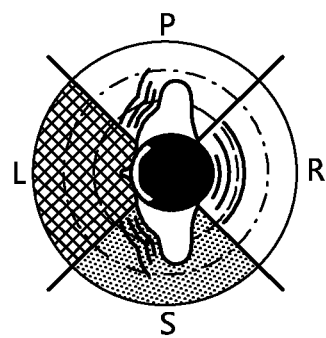

FIG. 3B shows in a schematic view a routine to adapt the threshold value of the non-movement timer during a sleep period. The threshold value is adapted to obtain a balanced pattern of sleep positions in a sleep period.

FIG. 3B shows in nine views I-IX successive moments T=0 to T=180 minutes during a sleep period. Each view illustrates four positions, i.e. a supine position S, a prone position P, a left-sided position and a right-sided position which are available to a user 100. Each view presents in a graph a threshold value for each determined position. The supine position is a non-desired sleep position. A threshold value for the supine position S is constant and not adapted. Here, the threshold value regarding the supine position S is set at a value close to zero, e.g. 1 minute which means that a user is quickly alerted during normal operation of the sleep position trainer when lying in the supine position.

The threshold values for the other sleep positions are variable and adaptable by the control unit of the sleep position trainer during a sleep period of the user. The graph presents an outer contour which represents a maximum value of a threshold value, and an origin of the graph represents a minimum value (zero-value) of the threshold value. A non-movement timer counts down from a set threshold value regarding a certain position when a user is lying in said position. At the same time, the threshold values for each position are adapted in dependence of a timed duration of non-movement in a certain position. This is illustrated in the successive views:

In view I, a user 100 starts sleeping at a moment T in a prone position (P, T=0).

In view II, the user 100 is sleeping for 30 minutes in the prone position (P, T=30). The graph shows a decrease of the threshold value for the non-movement timer from 90 minutes to 60 minutes.

In view III, the user 100 has moved to another sleep position. The user has moved to the right-sided position after sleeping 60 minutes in the prone position (R, T=60). From this moment of movement, the threshold value regarding the prone position will increase, while the threshold value regarding the right-sided position will decrease.

In view IV, the user 100 has changed position again. After 30 minutes in the right-sided position, the user has moved to the left-sided position (L, T=90). The graph shows the decrease of the threshold value regarding the right-side of position and the increase of the threshold value regarding the prone position.

In view V, after 15 minutes the user 100 is still in the left-sided position (L, T=105). Now, all threshold values are equal at 75 minutes. The threshold value regarding the left-sided position has decreased from 90 minutes to 75 minutes. The threshold value regarding the right-sided and prone position has increased from 60 minutes to 75 minutes.

In view VI, after a further 15 minutes, the user 100 is still in the left-sided position (L, T=120). At this moment, the threshold values regarding the right-sided and prone position reach their initially set threshold value and will no longer increase. The threshold value regarding the left-sided position is adapted from 75 minutes to 60 minutes. This means that in case the user would change position at this moment (T=120), the threshold values regarding the right-sided and prone position are adapted to 90 minutes, while the threshold value regarding the left-sided position is adapted to 60 minutes.

In view VII, the user 100 remains for a next duration of 30 minutes in the left-sided position. The threshold value regarding the left-sided position is further adapted and decreased by 30 minutes to a value of 30 minutes which means that the user is allowed to stay in the left-sided position for a remaining 30 minutes.

In view VIII, the user 100 has lied for ninety minutes in the left-sided position and has reached the end of the initially permitted duration for this position. The threshold value regarding the left-sided position is adapted to an adapted threshold value of zero minutes.

In view IX, a vibrational feedback is given to the user 100 to alert the user to move away from the left-sided position. As the threshold value for the left sided position is adapted to zero minutes, a next alert will be rendered after the first alert in case that the user moves back to the left-sided position too early. As explained with respect to views the threshold value regarding the left-sided position will continuously be adapted as long as the user remains in another position than the left-sided position. After ninety minutes in another position, the threshold value for the left-sided position will be reset to the initial threshold value.

Figure 4:
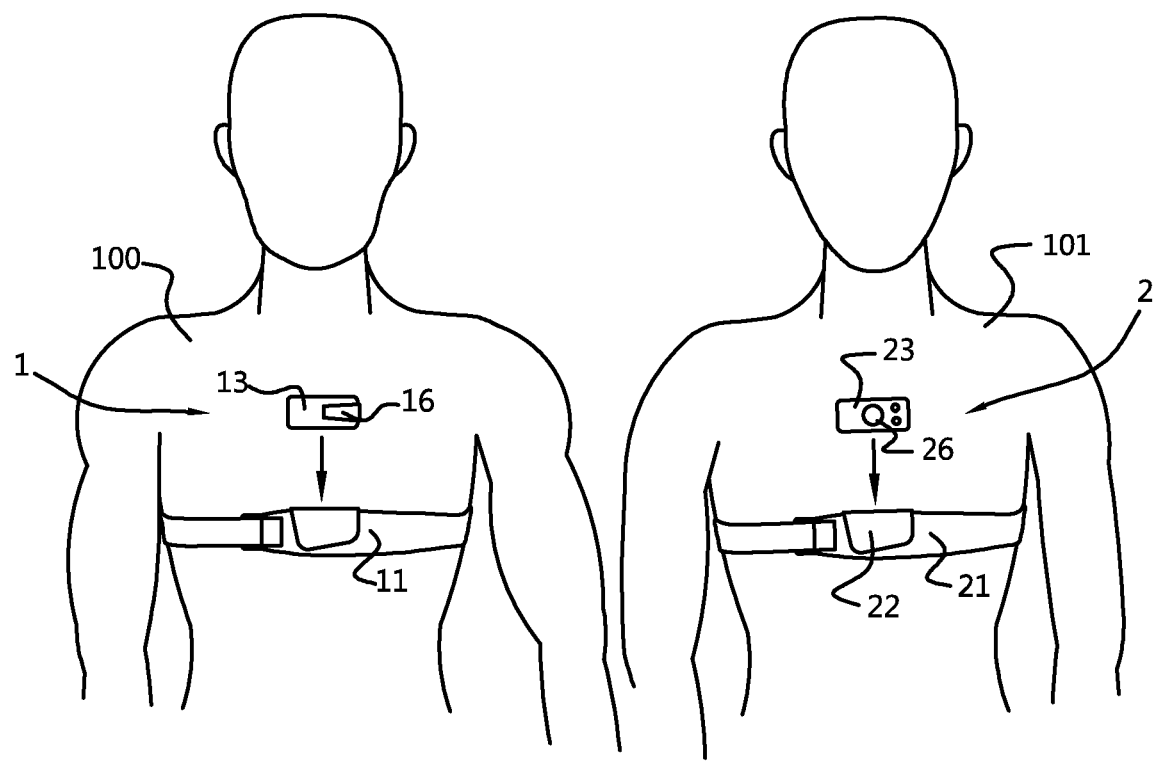
FIG. 4 shows in a schematic view a sleep position trainer and a bed partner device.

FIG. 4 shows in a schematic view a user 100 wearing a sleep position trainer 1 and a bed partner 101 wearing a bed partner device 2. The bed partner device 2 is attached to the bed partner 101 by a strap 21 with a pocket 22 for receiving a monitor 23. The bed partner device 2 is configured to cooperate with the sleep position trainer 1. The bed partner device 2 has a transmitter 16 for transmitting a device output signal, also called a bed partner signal, to the sleep position trainer 1 of the user 100. The sleep position trainer 1 is programmed to control the sleep position trainer based on a received bed partner signal. A presence of a bed partner may be stored in the user sleep data in the memory of the sleep position trainer. When the bed partner device 2 is activated, the sleep position trainer 1 is controlled in a bed partner modus in which due account is taken of a presence of a bed partner. In comparison with a normal modus, the sleep position trainer may select in the bed partner modus, moderate alert stimuli to prevent an awakening of the bed partner 101.

The bed partner device 2 includes a device control unit including a device control programme which is programmed to generate a device output signal based on at least one received device input signal from at least one device sensor. The at least one device sensor is configured for detecting a sleep related event of the bed partner. The at least one sensor is operatively connected to the device control unit to provide a device sensor signal to the device control unit.

Thus, according to an aspect of the invention a sleep position trainer 1 for improving a sleep quality of a user comprising a control unit CU to generate an output signal based on at least one received first input signal provided by at least one sensor S for detecting a sleep related event and an alert unit AU for providing an alert stimulus to the user after receiving an output signal from the control unit. A memory M for storing user sleep data USD. The user sleep data contains personal sleep data of an individual user. The control unit CU is programmed to derive an alert criterion c1 from the user sleep data to determine whether or not an alert stimulus is to be generated. The user sleep data contains sleep phase data of the individual user determining at least one sleep phase and corresponding risk data on an occurrence of a sleep disturbing event. An embodiment of this aspect is illustrated in FIG. 2.

Thus, according to an aspect of the invention a sleep position trainer 1 has a normal operational mode for alerting when a posture of the body detected by the position sensor 34 corresponds with an undesired body posture. The sleep position trainer further comprises a non-movement timer t1 for timing a non-movement period of the user wearing the sleep position trainer. An output signal is send to an alert unit in case that a posture of the body detected by a position sensor 34 corresponds with a body posture when a threshold value of the non-movement timer t1 of at least 15 minutes is exceeded. An embodiment of this aspect is illustrated in FIG. 3B

Thus, according to an aspect of the invention a sleep position trainer 1 for improving a sleep quality of a user comprising a control unit CU including a control programme which is programmed to generate an output signal based on at least one received first input signal provided by at least one sensor S for detecting a sleep related event and an alert unit AU for providing an alert stimulus to the user wearing the sleep position trainer apparatus after receiving an output signal from the control unit. A memory M for storing user sleep data USD which user sleep data contains personal sleep data of an individual user, wherein the control unit CU is programmed to derive an alert criterion c1 from the user sleep data to determine whether or not an alert stimulus is to be generated and whether or not the output signal is to be send to the alert unit. An embodiment of this aspect is illustrated in FIG. 4.

It is noted that the term "comprising" (and grammatical variations thereof) is used in this specification in the inclusive sense of "having" or "including", and not in the exclusive sense of "consisting only of".

Although the invention has been disclosed with reference to particular embodiments, from reading this description those of skilled in the art might appreciate a change or modification that may be possible from a technical point of view but which still do not depart from the scope of the invention as described above and claimed hereafter.

Modifications may be made to adapt a particular situation or material within the teaching of the invention and without departing from the essential scope thereof. It will be understood by those of skilled in the art that various changes may be made and equivalents may be substituted for elements thereof without departing from the scope of the invention. Therefore, the invention is not limited to the particular embodiments disclosed and illustrated in the above detailed description, but that the invention will include all embodiments falling within the scope of the appended claims.

| Reference signs list | | | |
|---|---|---|---|
| CU | control unit | t1 | non-movement timer |
| S | sensor | t2 | await timer |
| M | memory | | |
| USD | user sleep data | c1 | alert criterion |
| AU | alert unit | s1 | alert selector |
| V | vibrator | | |
| t | timer | | |
| 1 | sleep position trainer | 23 | device monitor |
| 10 | sleep position trainer | 26 | transmitter |
| 11 | strap | | |
| 12 | pocket | 3 | sensor |
| 13 | monitor | 31 | temperature sensor |
| 130 | monitor housing | 32 | microphone |
| 16 | bed partner receiver | 33 | heart rate sensor |
| | | 34 | position sensor |
| 2 | bed partner device | | |
| 21 | device strap | 100 | user |
| 22 | device pocket | 101 | bed partner |
| 301 | start | | |
| 302 | register event | | |
| 303 | define undesired position | | |
| 304 | determine position | | |
| 305 | evaluate position | | |
| 306 | stimulus for undesired position | | |
| 307 | start non-movement timer | | |
| 308 | evaluate duration of non-movement | | |
| 309 | stimulus for non-movement | | |
| 310 | evaluate position | | |
| 311 | threshold value adaption | | |

The invention claimed is:

1. Sleep position trainer apparatus which is configured to avoid an undesired posture during a sleep period, the sleep position trainer apparatus comprising:
a control unit (CU) which includes a control programme which is programmed to generate an output signal based on at least one received input signal;
at least one sensor (S) for detecting a sleep related event, which sensor is operatively connected to the control unit to provide a sensor signal as a first input signal to the control unit, wherein the sleep position trainer comprises a position sensor for detecting a body posture of a person wearing the sleep position trainer;
an alert unit (AU) for providing an alert stimulus to the user wearing the sleep position trainer apparatus, which alert unit is operatively connected to the control unit to receive the generated output signal from the control unit, whereafter the alert stimulus is generated;
wherein the sleep position trainer has a normal operational mode for alerting during a user's sleep period, in which normal operational mode the control unit generates an output signal to the alert unit, and the alert unit generates an alert stimulus when a posture of the body detected by the position sensor corresponds with at least one predefined undesired body posture, wherein the sleep position trainer further comprises a non-movement timer for timing a non-movement period of the user wearing the sleep position trainer, wherein the non-movement timer has a plurality of initial threshold values of at least 15 minutes and each corresponding to one of a plurality of body postures other than the at least one predefined undesired posture, wherein the control unit (CU) is programmed to determine, during a given sleep period, adapted threshold values corresponding to the plurality of body postures by, upon movement away from a selected body posture of the plurality of body postures, decreasing the initial threshold value corresponding to the selected body posture of the plurality of body postures based on time of non-movement in the selected body posture of the plurality of body postures, and increasing adapted threshold values corresponding to others of the plurality of body postures, up to a maximum of the initial threshold values corresponding to the others of the plurality of body postures, corresponding to an amount of time away from the others of the plurality of body postures, and wherein the control unit (CU) is programmed to send an output signal to the alert unit when a posture of the body detected by the position sensor corresponds with one of the plurality of body postures and the non-movement timer exceeds a lesser of the initial threshold value or the adapted threshold value corresponding to the one of the plurality of body postures.

2. Sleep position trainer according to claim 1, wherein the initial threshold values are predetermined threshold values.

3. Sleep position trainer according to claim 1, wherein non-movement of the user is detectable by the position sensor.

4. Sleep position trainer according to claim 1, wherein the control unit (CU) is programmed to select the alert stimulus which is to be generated by the alert unit from a group of alert stimuli that differ from each other.

5. Sleep position trainer according to claim 4, wherein one of the group of alert stimuli has a zero-intensity.

6. Sleep position trainer according to claim 4, wherein the control unit (CU) is programmed to select a selected one of the group of alert stimuli based on detection of an occurrence of a sleep disturbing event.

7. Sleep position trainer according to claim 4, wherein the control unit (CU) is programmed to select a selected one of the group of alert stimuli when the sensor detects a high risk on a sleep event.

8. Sleep position trainer according to claim 1, wherein the control unit (CU) is programmed to wait a predetermined period of time before sending the output signal to the alert unit.

* * * * *